United States Patent [19]

Poli et al.

[11] Patent Number: 5,369,131
[45] Date of Patent: Nov. 29, 1994

[54] ORAL, CUTANEOUS AND INTRAVAGINAL PHARMACEUTICAL COMPOSITIONS IN THE FORM OF FOAM

[75] Inventors: Stefano Poli; Germano Coppi; Cesare Busetti, all of Quinto de'Stampi-Rozzano, Italy

[73] Assignee: Poli Industria Chimica S.p.A., Milan, Italy

[21] Appl. No.: 63,954

[22] Filed: May 20, 1993

[51] Int. Cl.$^5$ ............................................. A61K 47/32
[52] U.S. Cl. .................................. 514/772.4; 424/45; 514/781; 514/772.3; 514/772.6; 514/885; 514/886; 514/945
[58] Field of Search ................. 424/400, 78.02, 45; 514/945, 885, 886

[56] References Cited

U.S. PATENT DOCUMENTS

| | | | |
|---|---|---|---|
| 4,588,581 | 5/1986 | Schmolka | 514/945 |
| 4,752,465 | 6/1988 | Mackles | 514/945 |
| 4,834,969 | 5/1989 | Grollier | 424/45 |
| 5,048,750 | 9/1991 | Tobler | 222/189 |
| 5,071,637 | 12/1991 | Pellico | 424/45 |
| 5,082,651 | 1/1992 | Healey et al. | 424/45 |

*Primary Examiner*—Thurman K. Page
*Assistant Examiner*—Amy Hulina
*Attorney, Agent, or Firm*—Griffin Butler Whisenhunt & Kurtossy

[57] ABSTRACT

A liquid pharmaceutical composition which can be administered as a foam by means of suitable supplying devices, without necessity of gas propeller, said composition consisting of:

a) one or more natural or synthetic ionic or non ionic, acid, basic or neutral surfactants;
b) a solvent or a solvent mixture;
c) an active ingredient or a combination of active ingredients;
d) optionally mucoadhesive or thermosetting polymers;
e) optional adjuvants or excipients.

10 Claims, No Drawings

ORAL, CUTANEOUS AND INTRAVAGINAL PHARMACEUTICAL COMPOSITIONS IN THE FORM OF FOAM

The present invention relates to pharmaceutical compositions in the form of foam.

Topical administration of active ingredients advantageously allows the maximum concentration of the drug directly near the biophase and contemporaneously avoids that the dispersion of the drug into tissues, which are not concerned with the presence of specific receptors or target organs, may cause unnecessary risks of toxicity or intolerance.

Recently, particular attention has been devoted to the development of compositions with high consistency, such as gel or ointment s or liquid compositions to be respectively applied by means of special adapters, such as nasal inhalators or sprays, vaginal douches or creams, etc. on the skin, or on the mucosae coating some body cavities.

Residence time of the composition at the site of application is critically affected by the consistency of the pharmaceutical composition, therefore a non optimized vehicle can negatively affect the therapeutic efficacy.

The problem is particularly critical in the case of intravaginal administration, since a poorly viscous composition is immediately diluted and expelled. To the contrary, a composition with high consistency, such as a cream, prevent s the diffusion of the active ingredient, thus limiting its activity to the site of deposition only. Antibacterial and antimycotic drugs are generally poorly absorbed and a blocked diffusion of the active ingredient gives rise to a partial therapeutic effect only. Further, a reduced drug diffusion may cause irritation and local side effect enhancement.

In the case of cutaneous administration, a high viscosity of the composition requires a stronger spreading, causing burning or pain if the tissues are irritated or damaged;

On the contrary a non viscous composition can be fastly eliminated from the site of application.

Object of the present invention is a liquid pharmaceutical composition, administered in the form of a foam by means of appropriate delivery devices, which comprises:
a) a natural or synthetic, ionic or non ionic surfactant or a surfactant mixture, having acid, basic or neutral characteristics
b) a solvent or a solvent mixture
c) a natural or synthetic active ingredient
d) optionally mucoadhesive or thermosetting polymers
e) optional adjuvants or excipients.

Compositions, which are similar to the above described ones, wherein the role of active ingredient is performed by surfactants and/or the solvents themselves, are a further object of the present invention. Such a composition can be useful in a topical intravaginal application when a therapeutic and/or hydrating, lubricating or protective effect is desired.

Conventional devices can be used to supply the compositions of the invention in the form of a foam. Particularly preferred devices are the ones described in EP-A-336188, which consist of a mixer wherein the liquid and air flows, properly regulated by the dimensions of holes, are forced through said holes, which are free or provided with a drawing tube, or similar ones .

For the cutaneous or intravaginal application, properly shaped cannulae can conveniently be inserted on the supplying spouts in order to facilitate the distribution and localization of the foam.

The surfactants according to the invention have the purpose to place themselves at the gas-liquid interface, assisting the inclusion into the liquid of an air or gas mass which is sufficient to create the desired foaminess. Among the synthetic surfactants, alkylamidobetaine, quaternary ammonium salts, poloxamers and the like are preferred, while among the natural ones, the phospholipids, and the like, are preferred. In any case, the percent content ranges from 0.01 to 20%.

According to a preferred embodiment of the invention, the foam compositions also contain mucoadhesive or thermosetting polymers, said polymers forming a film able to prolong the contact of the drug to the innermost mucosal sites.

The definition of mucoadhesive polymers, according to H. E. Junginger, Pharm. Ind. 53, (II), 1991, 1056-1065, include alginic acid and derivatives, jaluronic acid and derivatives , cellulose esters or ethers, carboxyvinylpolymers, acrylic copolymers, polyene copolymers, natural or synthetic gums, and polyglycuronic acid.

Typical thermosetting polymers include polyoxyethylene-polyoxypropylene copolymers.

The compositions of the invention may contain the mucoadhesive polymer in concentrations ranging from 0.05 to 5% w/w, preferably from 0.2 to 1%. The thermosetting polymer may be present in concentrations ranging from 8 to 18%, preferably from 10 to 15%.

The compositions of the invention can be administered not only by cutaneous and intravaginal route, but also by oral route.

Generally, the solvent of the composition is water or a water-ethanol mixture. Also other pharmaceutically acceptable solvents can be used.

Examples of active ingredients which can advantageously be included in the compositions of the invention, optionally combined between them, are antimycotic (ciclopirox olamine), antiinflammatory (diclofenac, benzidamine, piroxicam, tiaprofen, ketoprofen, tetridamine), corticosteroid (hydrocortisone and others), immunomodulator (Pidotimod and others), mucosecretolytic (sobrerol, carboxymethylcysteine), wound healing agents, vegetal extracts (Triticum vulgaris), amino acids, vitamins, xanthines (cyclopropylmethylxantine).

The active ingredients are contained in the compositions of the invention in percent amounts which depend from the nature of the active ingredient, but generally range from 0.01% to 20% w/v.

The compositions further contain excipients, such as preservatives, stabilizers, thickening agents, gelling agents, flavouring agents, dyes, cosolvents, structuring agents, etc., which will be selected according to the administration route and the kind of active ingredient.

The advantages of the invention are illustrated by the following pharmacological and clinical tests.

The foam containing 2% ciclopirox olamine (Example n. 1) for the intravaginal administration was tested in comparison with an aqueous composition containing the same active ingredient at the same concentration in the treatment of rat vaginal infection from *Candida albicans*.

Sprague Dawley (C. River) female rats weighing 100 g were ovariectomized and hysterectomized under nembutal anesthesia (40 mg/kg/i.p.).

After about three weeks from the operation, the rats were administered subcutaneously with 100 μg/day of estradiol vehicled in sesam oil, in order to induce pseudo estruation, which was monitored by vaginal smear exam with microscopy.

The rats which showed pseudo estruation were infected with $10^6$ Candida albicans cells, diluted in 0.2 ml of saline.

The treatment with 2% ciclopirox olamine vaginal foam or aqueous solution started three days after the infection and lasted 10 days. From the fourth day on, a vaginal withdrawal with sterile cotton swab was performed each morning. The swab was put into Sabouraud agar containing 20 IU/ml of penicillin G and 40 μg/ml of streptomycin for a microbiological test of the infective state.

The results reported on Table 1 show that both the ciclopirox olamine preparations are active towards the experimental infections but that the vaginal foam is much more faster than the aqueous composition due to the above mentioned characteristics.

In the case of cutaneous topical administration, surfactant high concentration and foam tenderness allow the medicament to be easily spreaded on the tissues and cutaneous annexes: foam breaking, which can be modulated according to the preparation parameters, allows spreading a homogenous and continuous solution film on the administration area without the necessity to force mechanically the dispersion of the medicament, contrarily to what happens for highly structured vehicles.

The 2% tetridamine topical foam (Example 2) was tested in comparison with an aqueous solution containing the same amount in the carrageen inflammation test and the analgesic activity test in the rat.

The antiinflammatory activity was determined on the carrageenin oedema (Winter et al, Proc. Soc. Exp. Biol. Med, 111, 544, 1962); the analgesic activity was tested on the same rats by means of the Randall and Selitto's test (Arch. Int. Pharmacodyn. 111, 409, 1957). Sprague Dawley (C. River) male rats, weighing 200 g, were injected with 2% carrageenin saline (0.1 ml/rat) in the upper right pad and treated three times with the tetridamine topical foam or topical solution (3 times at 20 minutes intervals). The volume of the inflamed pad was

TABLE 1

Ciclopirox olamine vaginal foam curative activity in comparison with the aqueous composition against vaginal infection from Candida albicans in the rat.

| Treatment | Female rats N. | N. of animals with negative microbiological test in day | | | | | | |
|---|---|---|---|---|---|---|---|---|
| | | 4. | 5. | 6. | 7. | 8. | 9. | 10. |
| Saline | 20 | 0/20 | 0/20 | 0/20 | 0/20 | 0/20 | 0/20 | 0/20 |
| 2% Ciclopirox olamine vaginal foam | 20 | 10/20 | 14/20 | 18/20 | 20/20 | 20/20 | 20/20 | 20/20 |
| 2% ciclopirox olamine aqueous solution | 20 | 5/20 | 7/20 | 10/20 | 13/20 | 17/20 | 20/20 | 20/20 |

The ciclopirox olamine vaginal foam formulation further proved to be actively tolerated in the one month toxicity tests performed on female rats and rabbits.

measured before and after 1, 2, 3, 4 or 5 hours the carrageenin injection with a plethysmograph (Basile, Italy).

TABLE 2

Topical antiinflammatory activity of tetridamine topical foam in comparison with the aqueous solution in carrageenin oedema.

| Treatment | Rats N. | Volume difference of inflamed pad against basal (ml) | | | | |
|---|---|---|---|---|---|---|
| | | 1 h | 2 h | 3 h | 4 h | 5 h |
| Saline | 10 | 0,48 ± 0,02 | 0,62 ± 0,03 | 0,69 ± 0,04 | 0,60 ± 0,05 | 0,38 ± 0,02 |
| 2% Tetridamine topical foam | 10 | 0,36 ± 0,02* | 0,22 ± 0,02* | 0,23 ± 0,03* | 0,24 ± 0,03* | 0,18 ± 0,02 |
| 2% Tetridamine aqueous solution | 10 | 0,39 ± 0,03* | 0,30 ± 0,03* | 0,40 ± 0,04* | 0,40 ± 0,04* | 0,30 ± 0,02 |

*$P < 0,01$ Dunnett's t vs. controls
$P < 0,01$ Student's t vs. aqueous solution

TABLE 3

Topical analgesic activity of tetridamine topical foam in comparison with the aqueous solution (Randall and Selitto's test).

| Treatment | Rats N. | Sensitivity to pain difference against basal (g) | | | | |
|---|---|---|---|---|---|---|
| | | 1 h | 2 h | 3 h | 4 h | 5 h |
| Saline | 10 | 85,6 ± 8,1 | 96,7 ± 10,1 | 75,8 ± 8,3 | 70,3 ± 9,5 | 55,4 ± 8,7 |

TABLE 3-continued

Topical analgesic activity of tetridamine topical foam in comparison with the aqueous solution (Randall and Selitto's test).

| Treatment | Rats N. | Sensitivity to pain difference against basal (g) | | | | |
|---|---|---|---|---|---|---|
| | | 1 h | 2 h | 3 h | 4 h | 5 h |
| 2% Tetridamine topical foam | 10 | 27,8 ± 4,5* | 25,6 ± 3,2* | 26,7 ± 4,5* | 28,3 ± 4,5* | 20,6 ± 4,6* |
| 2% Tetridamine aqueous solution | 10 | 36,7 ± 6,1* | 39,7 ± 4,3* | 40,6 ± 5,2* | 50,6 ± 6,2* | 43,2 ± 6,7* |

*P < 0,01 Dunnett's t vs. controls
P < 0,01 Student's t vs. aqueous solution

The sensitivity to pain of the inflamed pad was measured in g of weight before and after 1, 2, 3, 4 and 5 hours the carrageenin infection by means of a pain tester (Basile, Italy).

Table 2 shows that tetridamine topical foam has topical antiinflammatory activity higher and longer than the aqueous formulation one.

Similarly, Table 3 shows that the topical foam allows to obtain a stronger and longer analgesic activity in the rat. Those results are related to the foam composition which allows to obtain a better and longer absorption of the active ingredient tetridamine.

The tetridamine topical foam proved to be actively tolerated in one-month toxicity tests.

In the case of oral administration, the appearance of the dose to be administered, if appropriately flavoured, can make it more agreeable to patients having difficult swallowing, such as elder people or children, thus complying with the prescribed posology.

Pidotimod oral foam (Example 4) was tested within two group of patients in comparison with an aqueous solution having the same concentration. The first group included 40 children, male and female, aging between 6 and 10; the second group included 40 elder people, male and female, aging between 65 and 80.

The patient could take one of the two compositions according to choice, twice a day (8.00 a.m. and 8.00 p.m.). A week after, each patient had to select the preferred composition.

TABLE 4

Preference of the two Pidotimod compositions by two populations of patients.

| Compositions | Children (n. of patients which preferred) | Elders (n. of patients which preferred) |
|---|---|---|
| Pidotimod oral foam | 35/40 | 28/40 |
| Pidotimod aqueous solution | 05/40 | 12/40 |

Table 4 clearly shows that both populations of patients mostly preferred the oral foam composition.

The following examples further illustrate the invention.

EXAMPLE 1

200 g of ciclopirox olamine were dissolved in the minimum quantity of propylene glycol, then 3.5 l of an aqueous solution containing 0.2% of trimethylacetyl ammonium p-toluenesulfonate and 3.5% of fatty acids diethanolamide were added.

The solution was completed by adding perfume, natural vegetal extract and propylene glycol up to a 10 liter volume, adjusting pH to physiological value with lactic acid.

The above solution, once put into the vessel equipped with the appropriate device, supplied a soft and persisting foam, which could be spreaded on the skin for dermal mycosis treatment, or directed into the vaginal cavity by means of a cannula.

The same result was achieved by using the above composition with a gaseous propellant at ordinary pressure or a liquid one at high pressure, such as isobutane in a normal pressurized bottle.

EXAMPLE 2

10 g of tetridamine maleate, 30 g of alkylamidobetaine, 1 g of sodium methyl-p-hydroxybenzoate were dissolved in about 500 ml of deionized water. The clear solution was buffered at pH 4.5 with lactic acid and the volume was adjusted at 1 l. The solution was transferred into bottles provided with supplying system and vaginal cannula to allow a foam having antiinflammatory and antiphlogistic properties to be supplied.

EXAMPLE 3

100 g of tiaprofenic acid were salified in stoichiometric ratio with tromethamine in 500 g of an aqueous solution containing the suitable amounts of antimicrobic agents.

100 g of alcohol and 100 g of a quaternary surfactant of the betaine type were then added.

The solution was buffered at pH about 7, filtered and put into the suitable containers equipped with foam supplying valve. The so produced foam could easily be spreaded on the skin near articulations in order to assist the penetration of the active ingredient and to let the known antiinflammatory activity begin.

EXAMPLE 4

80 g of Pidotimod were dissolved by salification with 40 g of tromethamine in 500 g of a solution containing conventional sweeteners, antimicrobial agents, 150 g of sorbitol, 50 g of polyoxyethylene-polyoxypropylene copolymer and a suitable amount of flavouring agents. pH was adjusted to a slight acidic value and the final volume was adjusted to 1 l. The obtained solution was distributed into suitable dispensers equipped with foam generating valve. The foam, which was obtained with a simple manual pressure, was collected in a measure and used as vehicle for pediatric administration. In fact, the foam exhibited specific taste characteristics and a perfect edible property for the type of administrations wherein chewing or swallowing may be impaired. The same composition, put into an anodised aluminium gas bottle in the presence of a suitable quantity of propellant supplied from a normally used spray foam valve supplied a long lasting foam having a similar consistence.

EXAMPLE 5

A ethanolic solution containing 50 g of lecithin, 10 g of cholesterol and 20 g of ciclopirox olamine was mixed with 800 g of an alkylamidobetaine aqueous solution, protected against bacterial pollution with a suitable amount of sodium methyl-p-hydroxybenzoate and acidified with lactic acid.

The liposome suspension was then transferred into a bottle equipped with a foam generating valve and optionally equipped with a cannula for the endovaginal administration. A similar result was obtained transferring the above aqueous solution and the alcoholic one into a gas bottle, which had been pressurized with a sufficient amount of isobutane: operating the supplying button of a normal aerosol valve, evaporation of propellant was thus caused, therefore the alcohol, being the more volatile component, caused the immediate formation of a liposomial foam.

EXAMPLE 6

With a procedure similar to the one described in Example 2, tetridamine was substituted with 60 g of Triticum vulgate extract (dried residue equivalent to 200 mg/100 ml) obtaining a composition which, once put into a bottle equipped with a supplying valve could generate a foam which assisted the healing of the dermal tissues requiring reactivation.

EXAMPLE 7

With a procedure similar to the one de scribed in Example 4, instead of Pidotimod, a pool of amino acids consisting of 6 g of L-phosphoserine, 15 g of L-arginine hydrochloride, 2 g of L-phosphothreonine, 7.5 g of L-glutamine and 50 mg of vitamine B-12 were used as active ingredient.

An edible foam having characteristic flavour and very good swallowability was obtained.

EXAMPLE 8

Methylparaben and propylparaben were added to an aqueous solution of 10 g sodium diclofenac. 120 g of Lutrol F 127 (TM) were then added thereto and the final volume was adjusted to 1000 ml with water.

A solution was obtained able to form a soft foam which, when subjected to the body temperature, is visually thickened.

EXAMPLE 9

10 g of sodium hyaluronate and 50 g of hydroxyethylcellulose were added to the solution of Example 1. The solution, distributed in the bottle provided with a suitable dispenser, yields a foam having suitable consistency to be applied in the vaginal cavity where it remains with mucoadhesive properties.

We claim:

1. A liquid pharmaceutical composition which is propellant free and mechanically foamable, comprising:
    (1) at least one water soluble surfactant;
    (2) at least one pharmaceutically active ingredients;
    (3) a water-containing solvent; and
    (4) at least one of;
        (a) a mucoadhesive polymer selected from the group consisting of an alginic acid and derivatives, jaluronic acid and derivatives, cellulose esters or ethers, carboxyvinyl polymers, acrylic copolymers, polyene copolymers, natural or synthetic gums, polyglycuronic acid, and
        (b) a thermosetting polymer selected from the group consisting of polyoxyethylene-polyoxypropylene copolymers.

2. A composition according to claim 1, which is contained in a dosing bottle equipped with a foam supplying valve, consisting of a microdrilled device to which the solution and part of the air or gas contained in the bottle itself arrive separately by means of manual action on the bottle.

3. A composition according to claim 1 wherein the active ingredient is selected in the group consisting of antimycotic, antiinflammatory, immunomodulating, mucosecretolytic, wound-healing, repairer, antiphlogistic, anticongestion agents, amino acids, vitamins, corticosteroids and combination thereof.

4. A composition according to claim 1 which is orally administrable form.

5. A composition according to claim 1 wherein a foam is generatable with a valve-adaptor suitable for directing the foam into the vaginal cavity by means of a vaginal cannula.

6. A composition according to claim 1, wherein the active ingredient is selected from ciclopirox olamine, tetridamine base or a salt thereof, benzidamine base or a salt thereof, Pidotimod base or a salt or a derivative thereof, Triticum vulgare extract, hydrosoluble or liposoluble vitamins or amino acids in combination and/or mineral salts, carboxymethylcysteine and/or the salts or derivatives thereof, sobrerol, 3-cyclopropylmethylxanthine, hydrocortisone or the salts thereof, piroxicam or a complex with cyclodextrins thereof, ketoprofen or the salt thereof, diclofenac or the salt thereof.

7. A composition according to claim 6 wherein the active ingredient is contained in an amount ranging from 0.05% to 20% w/v.

8. A composition according to claim 6 wherein the active ingredient is contained in an amount ranging from 1% to 3% w/v.

9. A composition according to claim 1 wherein the concentration of the mucoadhesive polymer ranges from 0.05 to 5% w/w.

10. A composition according to claim 1 wherein the concentration of the thermosetting polymer ranges from 8 to 18% w/w.

* * * * *